United States Patent [19]

Kirmann

[11] Patent Number: Plant 6,028

[45] Date of Patent: Sep. 29, 1987

[54] GERANIUM PLANT NAMED DOLLY

[75] Inventor: Wolfgang Kirmann, Langenzersdorf, Austria

[73] Assignee: Mirko Vavra, Bisamberg, Austria

[21] Appl. No.: 811,166

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Dolly having light coral-red flower color fringed with white; ease of propagation and good rooting habit; very early flowering; good bud production at night temperatures up to 16° C., thus providing a long and continuous flowering period; and compact, self-branching growth habit.

2 Drawing Figures

The present invention comprises a new and distinct cultivar of geranium, botanically known as *Pelargonium domesticum,* and hereinafter referred to by the cultivar name Dolly.

Dolly is a product of a planned breeding program which had the objective of creating new geranium cultivars having early flowering response and long lasting flowers, good flower production, compact growth habit and light red flower color with a white margin.

Dolly was originated from a hybridization made by applicant in a controlled breeding program in Bisamberg, Austria in 1980. The female parent was Harlekin 78, a cultivar characterized by its light red flower color with white margin. The male parent of Dolly was a cultivar designated as seedling 3/78, having a very compact growth habit, good flower production and light red flower color with a light outer surface.

Dolly was discovered and selected as one flowering plant within the progeny of the stated cross by applicant on Apr. 1, 1981 in a controlled environment in Bisamberg, Austria.

The first act of asexual reproduction of Dolly was accomplished when vegetative cuttings were taken from the initial selection on Aug. 30, 1981 in a controlled environment in Bisamberg, Austria by a tehnician working under formulations established and supervised by Wolfgang Kirmann. Horticultural examination of selected units initiated in the spring of 1982 has demonstrated that the combination of characteristics as herein disclosed for Dolly are firmly fixed and are retained through successive generations of asexual reproduction.

Dolly has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Dolly, which in combination distinguish this geranium as a new and distinct cultivar.

1. A totally new coral-red flower color with the petals being fringed with white.
2. Very early flowering.
3. Propagates well with very good rooting habit.

4. Medium green foliage.
5. Compact, self-branching growth habit, resulting in the setting of many buds.
6. Buds are produced under normal greenhouse conditions (5000 Lux for 16 hours per day) at 14°-16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.
7. Dolly is unique with regard to the combined features of compactness, continuous flowering, floriferous habit, and coral-red flower color.

Of the many commercial cultivars known to the present inventor, the most similar in comparison to Dolly is Autumn Haze, a unpatented but commercial cultivar. In comparison to Autumn Haze, Dolly has a more compact growth habit, darker green foliage, earlier flowering and a more intense color.

The accompanying photographic drawings show typical flower and foliage characteristics of Dolly, with colors being as true as possible with illustrations of this type.

Sheet 1 is a perspective view of a potted plant of Dolly.

Sheet 2 is a black and white print showing the upper surface of immature and mature plants of Dolly.

In the following description color references are made to The Royal Horticultural Society Colour Chart (R.H.S.). The color values were determined at 9:00 a.m. on May 23, 1985 under 35,000 Lux light intensity in a greenhouse at Hillscheid, Federal Republic of Germany.

Classification:

*Botanical.* —*Pelargonium domesticum.*

*Commercial.*—Commonly referred to as a "Martha Washington" geranium, and having the cultivar name Dolly.

INFLORESCENCE

A. Umbel:

*Average diameter.*—Medium, 95–120 mm.

*Peduncle length.*—Normal.

*Pedicel length.*—Normal.

B. Corolla:

*Average diameter.*—65–80 mm; total inflorescence diameter is within the foliage.

*Form* .—Five-six petals.

*Color (general tonality from a distance of three meters).*—Light coral-red, fringed with white and variegated with a deeper and more intense red.

*Color (upper surface).*—48A-B, variegated with 47A, 46A on upper petals; fringed with white and having white at the base of the petals.

C. Bud:

*Shape.*—Oval.

*Color.*—White with pink.

D. Reproductive organs:

*Androecium.*—Reddish-yellow.

*Gynoecium.*—Five to six part.

E. Spring flowering response period: Very early.

F. Durability: Good.

PLANT

A. Foliage:

*Form.*—Zygomorphic with a nectar spur.

*Margin.*—Crenate to serrate, and indented.

*Color (upper surface).*—Medium green.

*Tolerance of Botrytis and soil fungi.*—Good.

B. General appearance and form:

*Internode length.*—Short.

*Branching pattern.*—Good.

*Height.*—Compact.

I claim:

1. A new and distinct cultivar of geranium named Dolly, as described and illustrated, and particularly characterized by its light coral-red flower color fringed with white; ease of propagation and good rooting habit; very early flowering; good bud production at night temperatures up to 16° C., thus providing a long and continuous flowering period; and compact, self-branching growth habit.

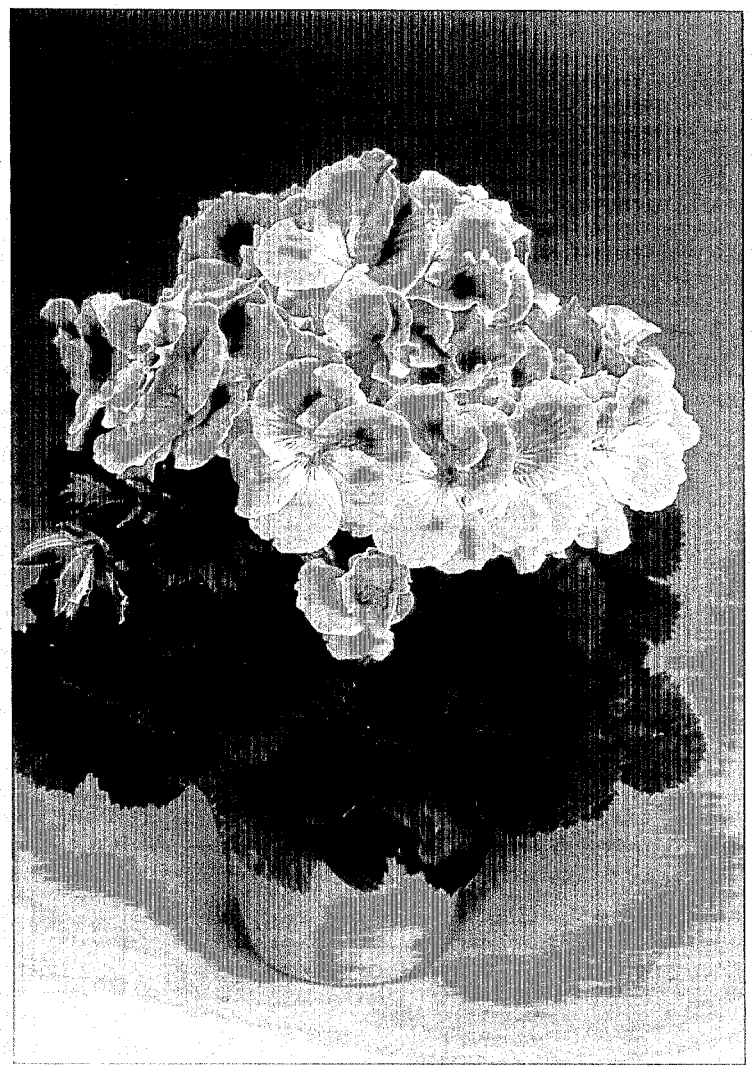

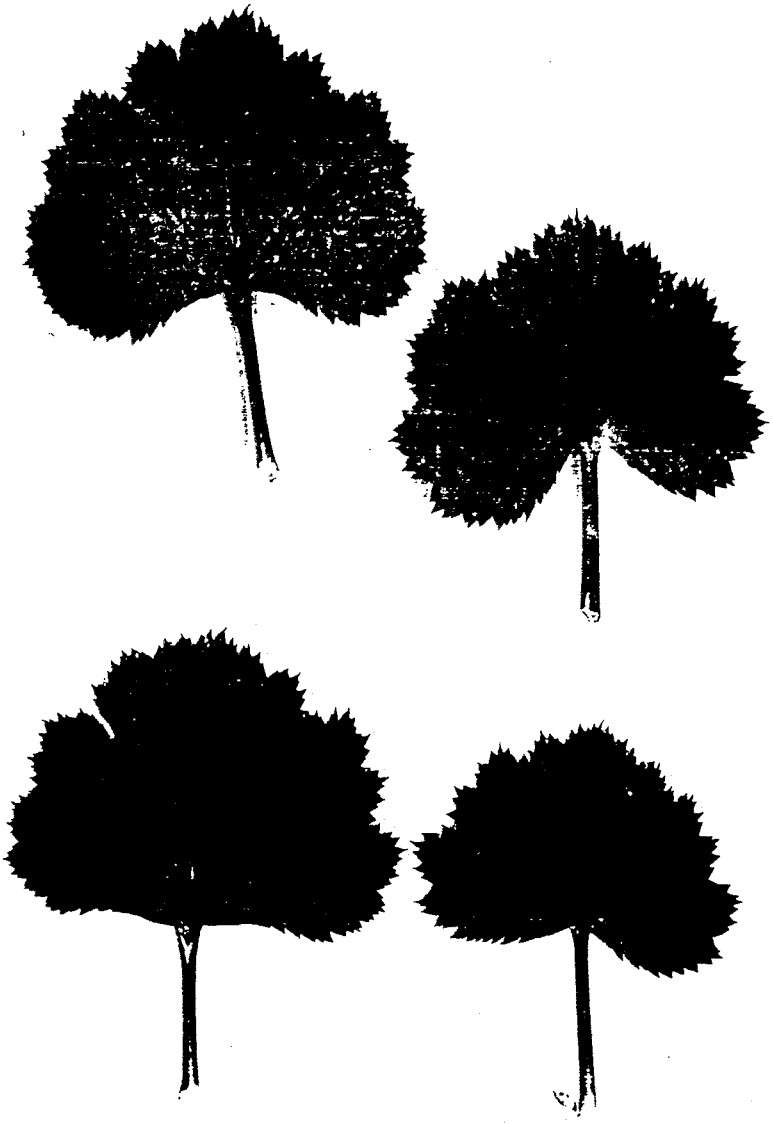

* * * * *